United States Patent
Ji et al.

(10) Patent No.: US 9,457,083 B2
(45) Date of Patent: Oct. 4, 2016

(54) LIPOSOME COMPOSITION FOR TREATING ACNE CONTAINING CONJUGATE OF LYSOPHOSPHATIDYLCHOLINE AND CHLORIN E6

(71) Applicant: H&A PHARMACHEM CO., LTD, Gyeonggi-do (KR)

(72) Inventors: Hong Geun Ji, Gyeonggi-do (KR); Hyo Gyoung Yu, Gyeonggi-do (KR); Young Rong Woo, Gangwon-do (KR); Jeong Dong Kim, Gyeonggi-do (KR); Se Hee Jo, Seoul (KR); Kun Na, Gyeonggi-do (KR); Hyung Park, Gyeonggi-do (KR)

(73) Assignee: H&A PHARMACHEM CO., LTD, Gyeonggi-Do (KR)

( * ) Notice: Subject to any disclaimer, the term of this patent is extended or adjusted under 35 U.S.C. 154(b) by 0 days.

(21) Appl. No.: 14/426,883

(22) PCT Filed: Jan. 22, 2015

(86) PCT No.: PCT/KR2015/000678
§ 371 (c)(1),
(2) Date: Mar. 9, 2015

(87) PCT Pub. No.: WO2016/068393
PCT Pub. Date: May 6, 2016

(65) Prior Publication Data
US 2016/0213781 A1  Jul. 28, 2016

(30) Foreign Application Priority Data
Oct. 28, 2014 (KR) .................. 10-2014-0147088

(51) Int. Cl.
| | |
|---|---|
| A61K 41/00 | (2006.01) |
| A61K 9/127 | (2006.01) |
| A61K 31/685 | (2006.01) |
| A61K 47/26 | (2006.01) |
| A61K 47/18 | (2006.01) |
| A61K 47/10 | (2006.01) |
| A61K 47/14 | (2006.01) |
| A61K 47/44 | (2006.01) |
| A61K 47/28 | (2006.01) |

(52) U.S. Cl.
CPC .......... *A61K 41/0071* (2013.01); *A61K 9/127* (2013.01); *A61K 31/685* (2013.01); *A61K 47/10* (2013.01); *A61K 47/14* (2013.01); *A61K 47/18* (2013.01); *A61K 47/26* (2013.01); *A61K 47/28* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 8,735,439 B2 * | 5/2014 | Park .................. | A61K 41/0071 514/410 |
| 2007/0020241 A1 | 1/2007 | Wilson et al. ............... | 424/93.6 |

FOREIGN PATENT DOCUMENTS

| | | | |
|---|---|---|---|
| KR | 10-0808630 | 2/2008 | ........... A61K 31/409 |
| KR | 10-2012-0093971 | 8/2012 | |
| KR | 10-2014-0035565 | 3/2014 | ............. A61K 31/40 |
| KR | 10-2014-0112622 | 9/2014 | ........... A61K 31/661 |
| WO | WO 2008/082200 | 7/2008 | ........... A61K 31/409 |
| WO | WO 2011/050102 | 4/2011 | ........... A61K 31/555 |

OTHER PUBLICATIONS

International Search Report (ISR) in PCT/KR2015/000678, dated Jun. 22, 2015 and published by WIPO on May 6, 2016 as WO 2016/068393.

* cited by examiner

*Primary Examiner* — Frederick Krass
*Assistant Examiner* — Celeste A Roney
(74) *Attorney, Agent, or Firm* — Harness, Dickey & Pierce, P.L.C.

(57) ABSTRACT

The present invention relates to a liposome composition comprising 0.001 to 5% by weight of conjugate of lysophatidylcholine and chlorin e6, 1 to 10% by weight of sucrose laurate, 0.1 to 5% by weight of sodium stearoyl glutamate, 1 to 10% by weight of PEG-5 rapeseed sterol, 1 to 20% by weight of medium-chain triglyceride, 1 to 10% by weight of vegetable oil, 0.1 to 5% by weight of sodium deoxycholate, 3 to 10% by weight of glycerin and the balance of water, and a skin care composition comprising the same. The liposome composition of the present invention is very effective in the treatment of acne.

7 Claims, 5 Drawing Sheets

LIPOSOME COMPOSITION FOR TREATING ACNE CONTAINING CONJUGATE OF LYSOPHOSPHATIDYLCHOLINE AND CHLORIN E6

CROSS-REFERENCE TO RELATED APPLICATIONS

This application is a national phase application of PCT Application No. PCT/KR2015/000678, filed on Jan. 22, 2015, which claims the benefit and priority to Korean Patent Application No. 10-2014-0147088, filed Oct. 28, 2014. The entire disclosures of the applications identified in this paragraph are incorporated herein by references.

TECHNICAL FIELD

The present invention relates to a liposome composition for treating acne containing conjugate of lysophophatidylcholine and chlorin e6. More particularly, the present invention relates to a liposome composition comprising 0.001 to 5% by weight of conjugate of lysophophatidylcholine and chlorin e6, 1 to 10% by weight of sucrose laurate, 0.1 to 5% by weight of sodium stearoyl glutamate, 1 to 10% by weight of PEG-5 rapeseed sterol, 1 to 20% by weight of medium-chain triglyceride, 1 to 10% by weight of vegetable oil, 0.1 to 5% by weight of sodium deoxycholate, 3 to 10% by weight of glycerin and the balance of water, and a skin care composition comprising the same.

BACKGROUND

Photodynamic therapy (PDT), which is also called as photochemotherapy, is a technique for treating incurable disease such as cancer without operation or treating skin disease such as acne by the use of a photosensitizer. There has been active study about PDT since the early twentieth century. Currently, PDT is used to increase immunocompetence in diagnosis and treatment of cancer, autologous bone marrow transplantation, antibiotics, AIDS treatment, skin graft or treatment of arthritis and the like, and so its applications have been gradually expanded. Specifically, PDT used in the treatment of cancer is a therapeutic method utilizing a principle in which a photosensitizer—which is a chemical compound showing sensitivity to light—is administered to the body; when it is exposed to external light, singlet oxygen or free radicals are generated via the chemical reaction by rich oxygen in the body and external light; and then such singlet oxygen or free radicals destroy various lesion sites or cancer cells by inducing cell death.

As photosensitizers used in PDT, porphyrin derivatives, chlorin, bacteriochlorin, phthalocyanine, 5-aminolevulinic acid derivatives and the like are known. Cyclic tetrapyrrole derivatives as photosensitizers also have properties for being utilized as agents for early diagnosis of tumor since they show fluorescence and phosphorescence according to their chemical properties as well as being selectively accumulated to cancer cells. In addition, metalloporphyrin, in which metal is bound to the interior of cyclic tetrapyrrole, shows various properties according to the kind of bound metal, thereby being applied to early diagnosis of tumor cells such as cancer cells by use of a diagnostic technique wherein metalloporphyrin is used as an MRI (magnetic resonance imaging) contrasting agent. 5-Aminolevulinic acid derivatives, which are the most widely known photosensitizers, have advantages wherein the method of use is simple, they can relatively easily penetrate into the skin due to small molecular weight, and they are safe with few side effects. Furthermore, one of the photosensitizers receiving attention is a chlorin-type photosensitizer, chlorin e6. As an example of the composition using chlorin e6, Korean Patent Application No. 10-2006-0136610 discloses antitumoric compositions for oral administration comprising chlorin e6 or a pharmaceutically acceptable salt thereof as an active ingredient.

As explained above, usage in the treatment of skin diseases such as acne was suggested as one of the applications of PDT, but no report has been made about its successful application.

DISCLOSURE OF INVENTION

Technical Problem

Therefore, the technical problem of the present invention is the provision of a composition exhibiting excellent effect on the treatment of acne by efficiently delivering the photosensitizer, chlorin e6 into the skin.

SUMMARY

To accomplish the above object, the present invention provides a liposome composition for the treatment of acne comprising 0.001 to 5% by weight of conjugate of lysophophatidylcholine and chlorin e6, 1 to 10% by weight of sucrose laurate, 0.1 to 5% by weight of sodium stearoyl glutamate, 1 to 10% by weight of PEG-5 rapeseed sterol, 1 to 20% by weight of medium-chain triglyceride, 1 to 10% by weight of vegetable oil, 0.1 to 5% by weight of sodium deoxycholate, 3 to 10% by weight of glycerin and the balance of water.

In addition, the present invention provides a skin care composition comprising the above liposome composition.

The present invention is described in detail hereinafter.

In the present invention, chlorin e6 (Ce6) forms a conjugate with lysophophatidylcholine (LPC). By conjugating chlorin e6 with lysophophatidylcholine, chlorin e6 can be efficiently transferred into the skin, and it can be helpful to form a liposome. Formation of the conjugate of lysophophatidylcholine and chlorin e6 can be obtained—for example, by the reaction of lysophophatidylcholine and chlorin e6 in the presence of catalysts, dicyclohexylcarbodiimide (DCC) and 4-dimethylaminopyridine (DMAP), as shown in the following Reaction Scheme 1.

[Reaction Scheme 1]

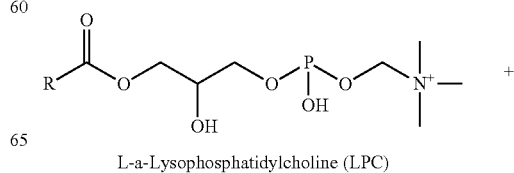

L-a-Lysophosphatidylcholine (LPC)

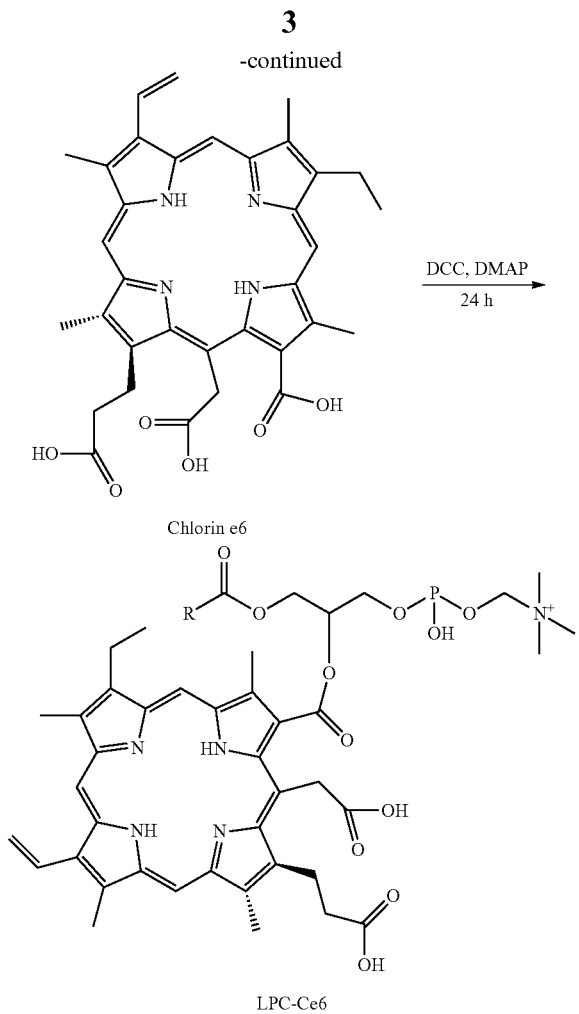

Chlorin e6

LPC-Ce6

In the above Reaction Scheme 1, R is $C_6$-$C_{22}$ saturated or unsaturated fatty acid chain. Hereinafter, the conjugate of lysophophatidylcholine and chlorin e6 is abbreviated as "LPC-Ce6."

The liposome composition according to the present invention comprises LPC-Ce6 in an amount of 0.001 to 5% by weight, preferably 0.01 to 3% by weight, and more preferably 0.1 to 2% by weight. In the present invention, if the amount of LPC-Ce6 is less than 0.001% by weight, the acne treatment effect of chlorin e6 (Ce6) may be weak, and if the amount of LPC-Ce6 is more than 5% by weight, it may be problematic in the formation of liposome.

The liposome composition according to the present invention comprises sucrose laurate as a non-ionic surfactant in an amount of 1 to 10% by weight, preferably 1.5 to 8% by weight, and more preferably 2 to 6% by weight. In the present invention, if the amount of sucrose laurate is less than 1% by weight or more than 10% by weight, it may be problematic in the formation of liposome.

The liposome composition according to the present invention comprises sodium stearoyl glutamate in an amount of 0.1 to 5% by weight, preferably 0.2 to 4% by weight, and more preferably 0.5 to 2% by weight. In the present invention, sodium stearoyl glutamate can increase the affinity of liposome for the skin. In the present invention, if the amount of sodium stearoyl glutamate is less than 0.1% by weight, it may be problematic in the affinity of liposome for the skin, and if the amount of sodium stearoyl glutamate is more than 5% by weight, it may be problematic in the formation of liposome.

The liposome composition according to the present invention comprises polyethylene glycol (PEG)-5 rapeseed sterol in an amount of 1 to 10% by weight, preferably 1.5 to 8% by weight, and more preferably 2 to 6% by weight. In the present invention, PEG-5 rapeseed sterol can help the formation of liposome vesicles and impart stability to liposome bilayer. In the present invention, if the amount of PEG-5 rapeseed sterol is less than 1% by weight, the effect of PEG-5 rapeseed sterol at the time of forming liposome may be weak, and if the amount of PEG-5 rapeseed sterol is more than 10% by weight, it may render liposome unstable.

The liposome composition according to the present invention comprises medium-chain triglyceride (MCT) in an amount of 1 to 20% by weight, preferably 3 to 15% by weight, and more preferably 5 to 12% by weight. In the present invention, medium-chain triglyceride—which is 6-12 carbon fatty acid esters of glycerol—helps the penetration of liposome into the skin. In the present invention, if the amount of medium-chain triglyceride is less than 1% by weight, it may be problematic in the penetration of liposome into the skin, and if the amount of medium-chain triglyceride is more than 20% by weight, it may be problematic in the formation of liposome.

The liposome composition according to the present invention comprises vegetable oil in an amount of 1 to 10% by weight, preferably 1.5 to 8% by weight, and more preferably 2 to 6% by weight. In the present invention, vegetable oil plays a role in helping the penetration of liposome into the skin. In the present invention, examples of vegetable oil include, but are not limited to, sunflower seed oil, olive oil, camellia oil, macadamia oil, castor oil, jojoba oil, almond oil, apricot kernel oil, green tea oil, meadowfoam seed oil, argan oil or a mixture thereof. In the present invention, if the amount of vegetable oil is less than 1% by weight, it may be problematic in the penetration of liposome into the skin, and if the amount of vegetable oil is more than 10% by weight, it may be problematic in the formation of liposome.

The liposome composition according to the present invention comprises sodium deoxycholate in an amount of 0.1 to 5% by weight, preferably 0.2 to 3% by weight, and more preferably 0.3 to 2% by weight. In the present invention, sodium deoxycholate makes liposome flexible, so that liposome can easily pass through stratum corneum lipids. In the present invention, if the amount of sodium deoxycholate is less than 0.1% by weight, it may be problematic in the penetration of liposome into the skin, and if the amount of sodium deoxycholate is more than 5% by weight, liposome may be unstable.

The liposome composition according to the present invention comprises glycerin and water as solvents. The liposome composition according to the present invention comprises glycerin in an amount of 3 to 10% by weight, preferably 5 to 9% by weight, and more preferably 6 to 8% by weight. In the present invention, water may be comprised in an amount of—for example, 25 to 92.999% by weight, or 56 to 82.1% by weight.

The liposome composition according to the present invention may further comprise additives such as excipient, sweetener, flavor and the like, depending on need.

In the present invention, the diameter of liposome is preferably 100 to 300 nm.

According to another aspect of the present invention, a skin care composition comprising the liposome composition of the present invention is provided. In the present invention, examples of skin care composition include, but are not limited to, toner, lotion, body lotion, cream, essence and the like. The skin care composition comprises preferably 1 to 30% by weight of the liposome composition according to the present invention. In the present invention, if the skin care composition comprises the liposome composition in an amount of less than 1% by weight, the acne treatment effect of chlorin e6 may be weak, and if the amount of the liposome composition is greater than 30% by weight, it may be economically undesirable since increasing the acne treatment commensurately with the adding amount would not be expected.

Advantageous Effects of Invention

The liposome composition according to the present invention can effectively treat acne by stably and efficiently transferring chlorin e6 into the skin.

DRAWINGS

DETAILED DESCRIPTION

Figure 1:
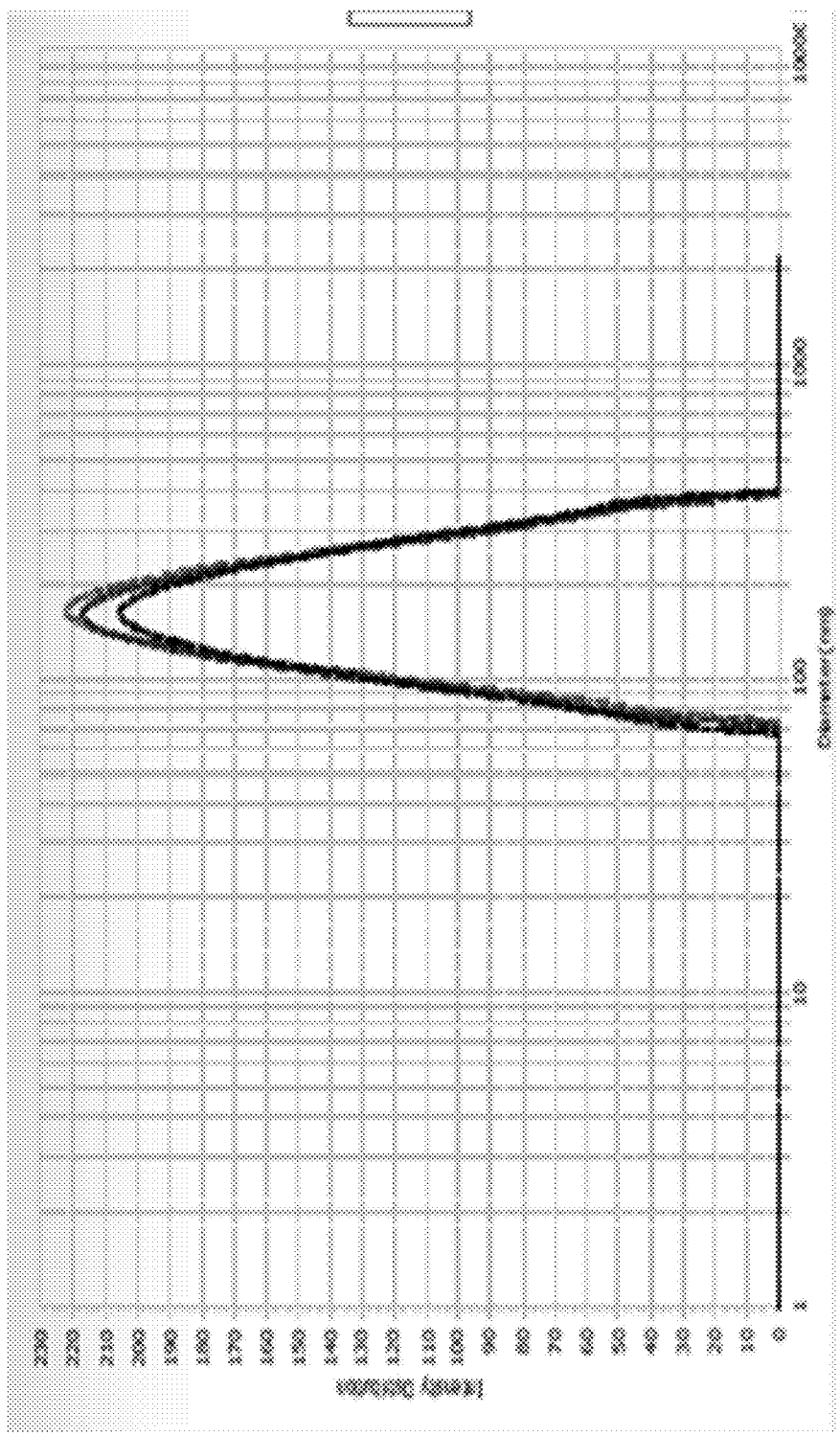
FIG. 1 is a result of measuring the diameter of the liposome particles of the present invention by the use of Photal ELS-Z.

Hereinafter, the present invention is explained in more detail with the following examples. However, it must be understood that the protection scope of the present invention is not limited to the examples.

Preparation Example

Preparation of LPC-Ce6

10 mg of L-α-lysophophatidylcholine was dissolved in 10 ml of anhydrous dichloromethane. 10 mg of chlorin e6 (Ce6) and catalysts, 5.35 mg of N,N'-dicyclohexylcarbodiimide (DCC) and 5.35 mg of 4-dimethylaminopyridine (DMAP) were added to 10 ml of anhydrous dichloromethane and agitated for 4 hours. The solution in which Ce6 is dissolved in anhydrous dichloromethane and the solution in which L-α-lysophophatidylcholine is dissolved in anhydrous dichloromethane were then mixed, and the reaction was carried out at room temperature for 48 hours. After reaction, anhydrous dichloromethane was evaporated in a 40° C. evaporator for 30 minutes. The obtained conjugate was cold stored at 4° C. until use.

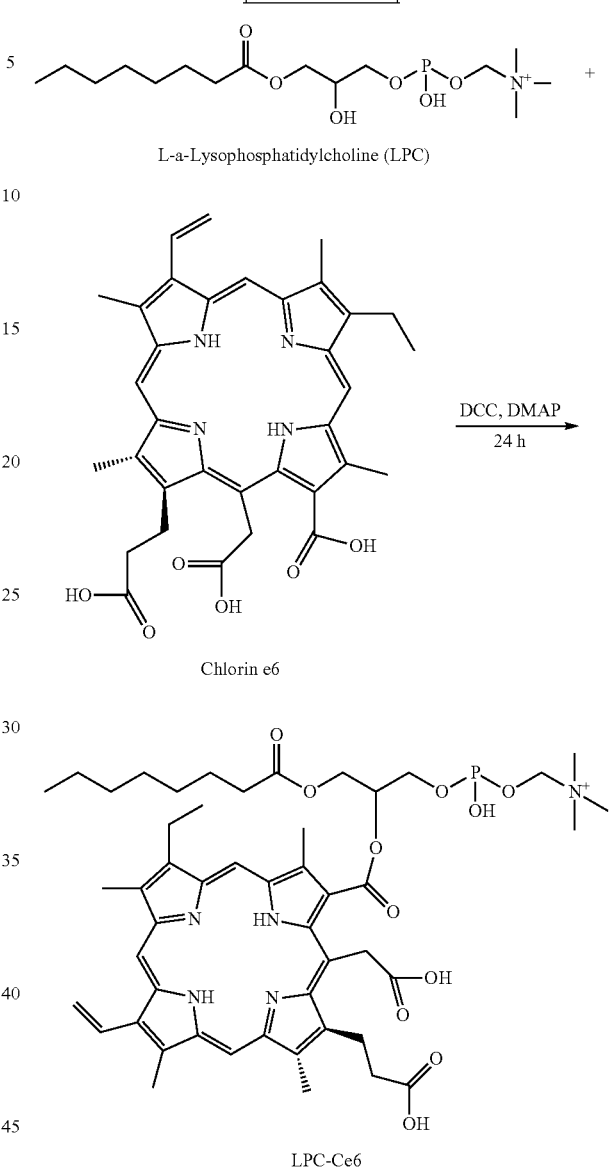

[Reaction Scheme 2]

L-a-Lysophosphatidylcholine (LPC)

Chlorin e6

LPC-Ce6

Example 1

Preparation of Liposome Composition Containing LPC-Ce6

Sucrose laurate, PEG-5 rapeseed sterol, sunflower seed oil and medium-chain triglyceride were dissolved at 80° C. Glycerin, distilled water, sodium deoxycholate and sodium stearoyl glutamate were heated to 80° C. or more and incorporated into an oil phase, and then wetted at 100° C. for 1 hour. The resulting mixture was cooled to 40° C., and LPC-Ce6 was then added thereto and emulsified. The resulting mixture was continuously passed three (3) times through a high-pressure microfluidizer at 1,000 bar, followed by cooling and deaeration to obtain liposome composition.

TABLE 1

| Ingredient | Content (% by weight) |
| --- | --- |
| LPC-Ce6 | 1 |
| Sucrose laurate | 3 |
| Sodium stearoyl glutamate | 0.8 |
| PEG-5 rapeseed sterol | 5 |
| Medium-chain triglyceride | 10 |
| Sunflower seed oil | 5 |
| Sodium deoxycholate | 0.5 |
| Glycerin | 7 |
| Distilled water | 67.7 |
| Total amount | 100 |

Comparative Example

Preparation of Emulsion Containing LPC-Ce6

Each ingredient was incorporated into a vessel according to the constitutional composition of the following Table 2 and then dissolved at 80° C. The resultant was mixed for 5 minutes by the use of a homo-mixer, and then cooled and deaerated to obtain emulsions.

TABLE 2

| Ingredient | Content (% by weight) |
| --- | --- |
| LPC-Ce6 | 1 |
| Sucrose laurate | 3 |
| Sodium stearoyl glutamate | 0.8 |
| PEG-5 rapeseed sterol | 5 |
| Medium-chain triglyceride | 10 |
| Sunflower seed oil | 5 |
| Polyglyceryl-3 methylglucose distearate | 3 |
| Sodium deoxycholate | 0.5 |
| Glycerin | 7 |
| Distilled water | 64.7 |
| Total amount | 100 |

Example 2

Preparation of Toner Containing Liposome

A toner containing the liposome of the present invention was prepared according to the constitutional composition of the following Table 3.

TABLE 3

| Ingredient | Content (% by weight) |
| --- | --- |
| Liposome of Example 1 | 3 |
| Glycerin | 7 |
| Glycan | 1 |
| Polyglutamic acid | 1 |
| Distilled water | 88 |
| Total amount | 100 |

Example 3

Preparation of Lotion Containing Liposome

A lotion containing the liposome of the present invention was prepared according to the constitutional composition of the following Table 4.

TABLE 4

| Ingredient | Content (% by weight) |
| --- | --- |
| Liposome of Example 1 | 10 |
| Polyglyceryl-3 stearate/behenate | 2 |
| Stearic acid | 0.8 |
| Macadamia oil | 4 |
| Capric/caprylic triglyceride | 3 |
| Silicone oil (6Cs) | 4 |
| Glycerin | 5 |
| Carbopol | 0.1 |
| Distilled water | 71.1 |
| Total amount | 100 |

Example 4

Preparation of Body Lotion Containing Liposome

A body lotion containing the liposome of the present invention was prepared according to the constitutional composition of the following Table 5.

TABLE 5

| Ingredient | Content (% by weight) |
| --- | --- |
| Liposome of Example 1 | 8 |
| Sorbitan stearate/sucrose cocoate | 3 |
| Liquid paraffin | 5 |
| Capric/caprylic triglyceride | 2 |
| Olive oil | 2 |
| Glycerin | 10 |
| Distilled water | 70 |
| Total amount | 100 |

Example 5

Preparation of Cream Containing Liposome

A body lotion containing the liposome of the present invention was prepared according to the constitutional composition of the following Table 6.

TABLE 6

| Ingredient | Content (% by weight) |
| --- | --- |
| Liposome of Example 1 | 15 |
| Polyglyceryl-3 methylglucose distearate | 5 |
| Cetearyl alcohol | 1.5 |
| Capric/caprylic triglyceride | 5 |
| Olive oil | 4 |
| Dimethicone oil (150 Cs) | 1 |
| Glycerin | 5 |
| Carbopol | 0.45 |
| Distilled water | 63.05 |
| Total amount | 100 |

Example 6

Preparation of Essence Containing Liposome

An essence containing the liposome of the present invention was prepared according to the constitutional composition of the following Table 7.

TABLE 7

| Ingredient | Content (% by weight) |
|---|---|
| Liposome of Example 1 | 20 |
| Xanthan gum | 0.2 |
| Hyaluronic acid | 1 |
| Polyglutamic acid | 5 |
| Sodium EDTA | 0.05 |
| Silica | 1 |
| PEG-1500 | 3 |
| Glycerin | 5 |
| Distilled water | 64.75 |
| Total amount | 100 |

Experimental Example 1

Measurement of Particle Size Distribution of Liposomes

The particle size distribution of the liposomes prepared in Example 1 was measured by the use of Photal ELS-Z, and the result is represented in FIG. 1. From the result of the measurement, it can be known that the average particle size is 153.9 nm.

Experimental Example 2

Measurement of Stability of Liposomes

Figure 2:
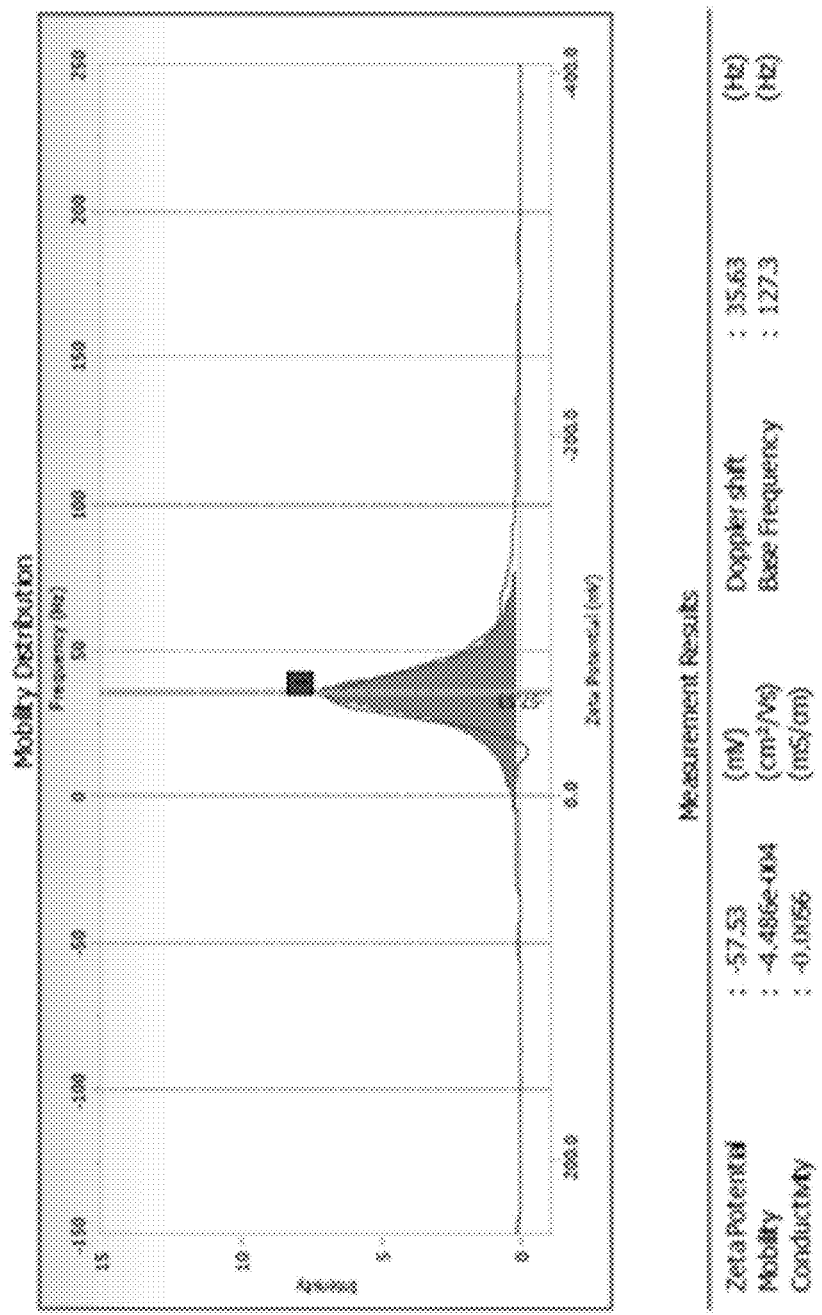
FIG. 2 is a result of measuring the zeta potential of the liposomes of the present invention by the use of Photal ELS-Z.

To measure the stability of liposomes prepared in Example 1, zeta potential was measured by the use of Photal ELS-Z, and the result is represented in FIG. 2. From the result of the measurement, it can be known that the potential of particle is −57.53 mV, and the liposomes are stable.

Experimental Example 3

Measurement of Stability of Liposomes

Figure 3:
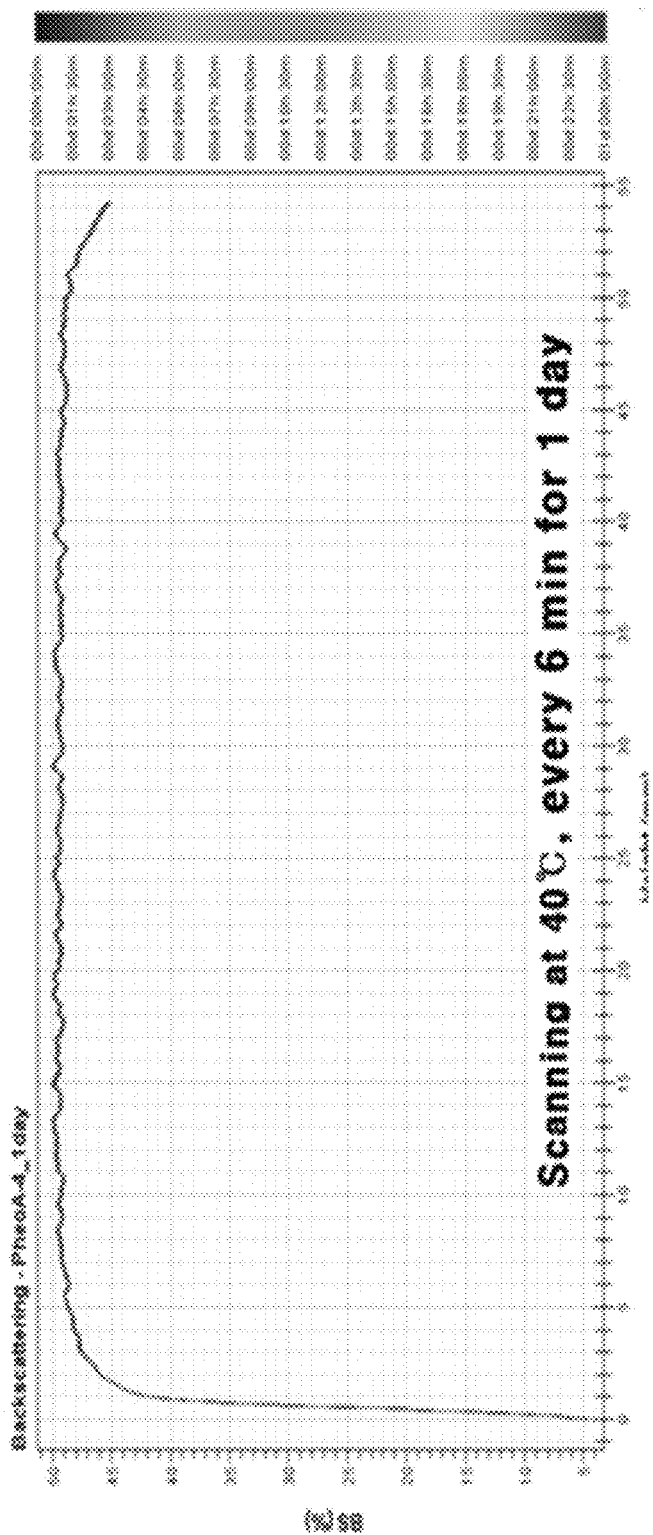
FIG. 3 is a result of measuring the stability of the liposomes of the present invention.

The stability of liposomes prepared in Example 1 was measured by the use of Turbiscan. As a result, the stability of the liposomes was confirmed (FIG. 3).

Experimental Example 4

Photography of Liposomes

Figure 4:
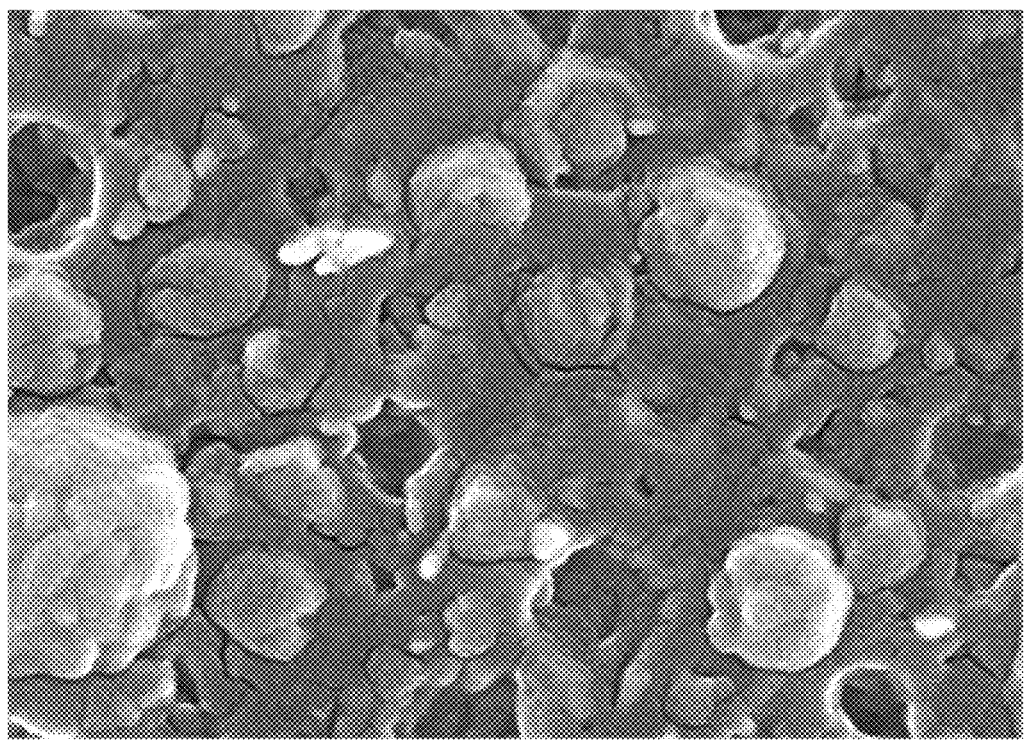
FIG. 4 is a cryo-electron microscopy photograph of the liposome composition of the present invention.

A photograph of the liposomes prepared in Example 1 was taken. Due to very fine particle size, it was impossible to take a photograph by a general optical microscope. Therefore, a cryo-electron microscopy photograph (JEM 1010, JEOL Ltd., Japan) was taken (FIG. 4). From FIG. 4, it can be known that liposomes are well formed with uniform size.

Experimental Example 5

Test for Promoting Transdermal Absorption

An 8-week-old female hairless guinea pig (strain IAF/HA-hrBR) was used. The abdominal skin of the guinea pig was cut and mounted to a Franz-type diffusion cell (Lab Fine Instruments, Korea). 50 mM phosphate buffer (pH 7.4, 0.1M NaCl) was added to a receptor cell (5 ml) of the Franz-type diffusion cell. A diffusion cell was then mixed and diffused at 600 rpm, 32° C., and 50 μl of liposomes of Example 1 and emulsions of the Comparative Example, respectively, were added to donor cells. Absorption and diffusion were carried out according to the predetermined time, and the area of the skin where the absorption and diffusion were carried out was 0.64 cm². After finishing the absorption and diffusion of the active ingredient, the residues—which were not absorbed and remained on the skin—were cleaned with dried Kimwipes™ or 10 ml of ethanol. The skin in which the active ingredient is absorbed and diffused was homogenized by the use of a tip-type homogenizer, and chlorin e6 absorbed into the skin was then extracted with 4 ml of dichloromethane. The extract was then filtrated with a 0.45 μm nylon membrane filter. The content of chlorin e6 was measured by high-performance liquid chromatography with the following conditions, and the results are represented in Table 8.

TABLE 8

| | Transdermal absorption (μg) | Rate of increase |
|---|---|---|
| Liposome of Example 1 | 1.44 | 3.6-fold |
| Emulsion of Comparative Example | 0.40 | — |

A) Column: C18 (4.6 × 200 mm, 5 μm)
B) Mobile phase: methanol:hexane = 2:1
C) Flow rate: 0.8 ml/min
D) Detector: UV 275 nm As can be seen from Table 8, the liposome of the present invention shows excellent transdermal absorption, as compared with general emulsion.

Experimental Example 6

Measurement of Acne Treatment Effect

Figure 5:
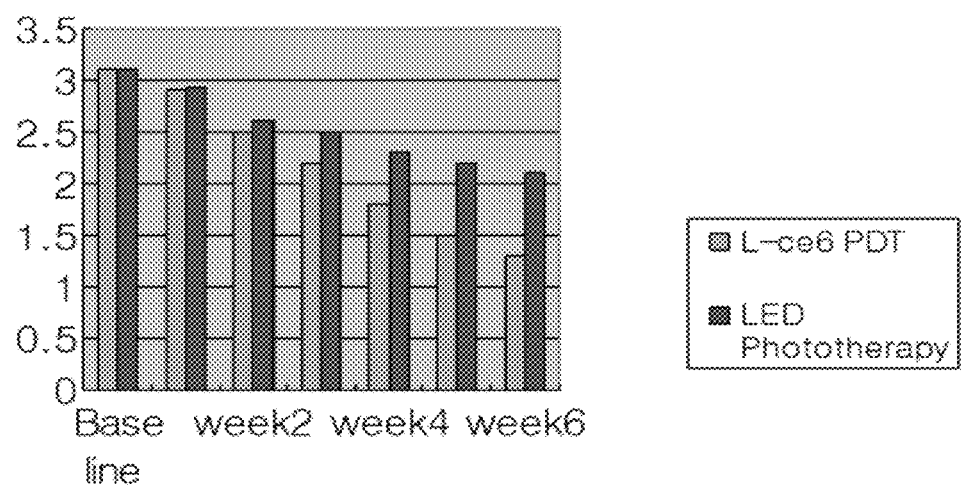
FIG. 5 is a graph representing the acne treatment effect of the liposome composition of the present invention in comparison with LED phototherapy.
Figure 6:
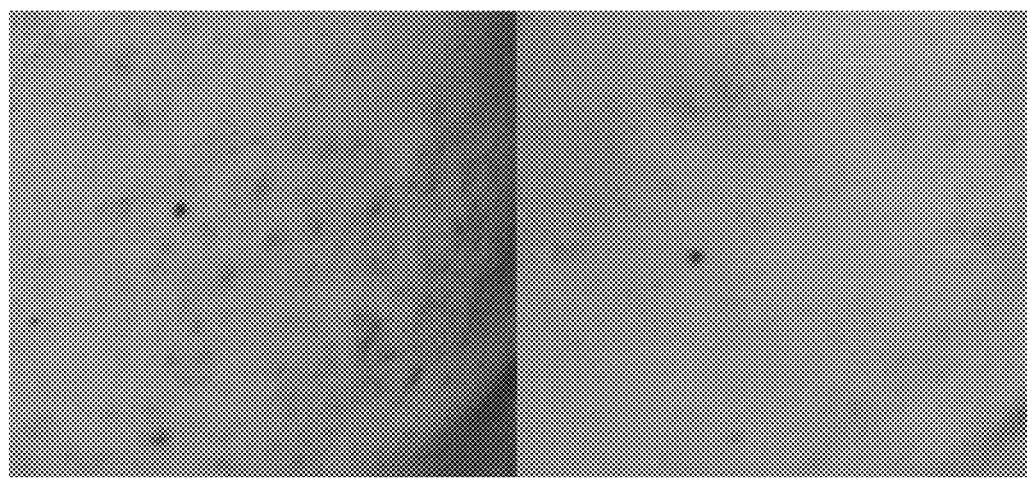
FIG. 6 is a set of photographs showing the acne treatment effect of the liposome composition of the present invention. The left photograph is before treatment, and the right photograph is 2 weeks after treatment.

Twenty (20) men and women in their teens and twenties having severe acne were divided into two groups (ten persons per group). In one group, the lotion of Example 3 was applied three times per day, and in the other group LED phototherapy was performed. In week 2, week 4 and week 6 after treatment initiation, the treatment effect was evaluated with the naked eye. Evaluation was graded from 0 (no acne) to 5 (most severe acne), and the results are represented in FIG. 5. FIG. 6 is a set of photographs of a test subject in the group—in which liposome containing chlorin e6 was used—taken before the treatment and in week 2 after treatment.

As can be seen from FIGS. 5 and 6, the liposome containing chlorin e6 of the present invention is very effective in the treatment of acne.

What is claimed is:

1. A liposome composition for the treatment of acne comprising:
   0.001 to 5% by weight of conjugate of lysophophatidylcholine and chlorin e6,
   1 to 10% by weight of sucrose laurate,
   0.1 to 5% by weight of sodium stearoyl glutamate,
   1 to 10% by weight of polyethylene glycol-5 rapeseed sterol,
   1 to 20% by weight of medium-chain triglyceride,
   1 to 10% by weight of vegetable oil,
   0.1 to 5% by weight of sodium deoxycholate,
   3 to 10% by weight of glycerin and the balance of water.

2. The liposome composition according to claim 1, wherein the conjugate of lysophophatidylcholine and chlorin e6 is the following Formula 1:

Formula 1

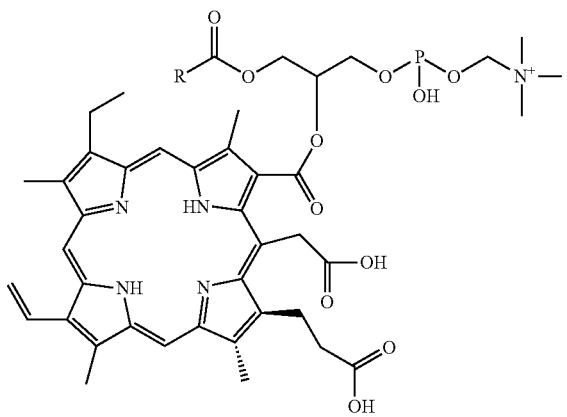

wherein R represents $C_6$-$C_{22}$ fatty acid chain.

3. The liposome composition according to claim 1, wherein the vegetable oil is selected from the group consisting of sunflower seed oil, olive oil, camellia oil, macadamia oil, castor oil, jojoba oil, almond oil, apricot kernel oil, green tea oil, meadowfoam seed oil, argan oil or a mixture thereof.

4. The liposome composition according to claim 1, which comprises 0.1 to 2% by weight of conjugate of lysophophatidylcholine and chlorin e6, 2 to 6% by weight of sucrose laurate, 0.5 to 2% by weight of sodium stearoyl glutamate, 2 to 6% by weight of polyethylene glycol-5 rapeseed sterol, 5 to 12% by weight of medium-chain triglyceride, 2 to 6% by weight of vegetable oil, 0.3 to 2% by weight of sodium deoxycholate, 6 to 8% by weight of glycerin and 56 to 82.1% by weight of water.

5. The liposome composition according to claim 1, wherein the diameter of the liposome is 100 to 300 nm.

6. A skin care composition comprising the liposome composition for the treatment of acne according to claim 1.

7. The skin care composition according to claim 6, which comprises 1 to 30% by weight of the liposome composition for the treatment of acne.

* * * * *